United States Patent [19]

Tanei et al.

[11] Patent Number: 4,481,813
[45] Date of Patent: Nov. 13, 1984

[54] DEW SENSOR

[75] Inventors: Hirayoshi Tanei, Tokyo; Shoichi Iwanaga; Akira Ikegami, both of Yokohama; Hiroshi Otsu, Mito; Hiromi Isonae, Nakaminato, all of Japan

[73] Assignee: Hitachi, Ltd., Tokyo, Japan

[21] Appl. No.: 436,944

[22] Filed: Oct. 27, 1982

[30] Foreign Application Priority Data

Oct. 28, 1981 [JP] Japan ................................ 56-171414

[51] Int. Cl.³ ........................................... G01N 27/12
[52] U.S. Cl. .................................... 73/336.5; 73/73; 338/35
[58] Field of Search ........................ 73/73, 336.5, 336; 338/34, 35

[56] References Cited

U.S. PATENT DOCUMENTS 3,671,913  6/1972  Mamiya et al. ............... 73/336.5 X
4,041,437  8/1977  Matsuura et al. .............. 73/336.5 X
4,167,725  9/1979  Shimizu et al. ........................ 338/35
4,245,506  1/1981  Meiklejohn ........................... 73/336

FOREIGN PATENT DOCUMENTS 51880    4/1977  Japan .................... 73/336.5
156690  12/1979  Japan ....................... 338/35
543908   4/1977  U.S.S.R. ................ 73/336.5

*Primary Examiner*—Gerald Goldberg
*Assistant Examiner*—Hezron Williams
*Attorney, Agent, or Firm*—Antonelli, Terry & Wands

[57] ABSTRACT

A dew sensor of direct current type and resistance-lowering type with increasing humidity for quick and sharp detection of dewing is provided, which comprises a pair of counterposed electrodes, humidity-sensitive layer of insulating porous metal oxide with a porosity of 20 to 60% provided on and between the counterposed electrodes, and an organic polymer coating layer having a thickness of 0.05 to 2 μm provided on the humidity-sensitive layer.

11 Claims, 5 Drawing Figures

DEW SENSOR

BACKGROUND OF THE INVENTION

This invention relates to a dew sensor for detecting deposition of dews, that is, dewing, through a change in electric resistance.

According to the so far known methods, deposition of dews is detected by (1) optical changes in light reflection or water absorption spectra, (2) changes in resonance frequency of piezo-resonator, or decrease in Q, (3) changes in capacity, or (4) changes in electric resistance, among which the method (1) requires a highly precise optical system which is hard to carry and expensive, and is not readily applicable to the domestic appliances and the methods (2) and (3) have a complicated detection electric circuit, whereas the method (4) based on changes in electric resistance has been regarded as most preferable because of the relatively simple detection circuit.

The method (4) has two types, i.e. an alternating current type and a direct current type, depending upon the species of a power source for the contemplated detection circuit, and also has an electric resistance-increasing type [for example, National Technical Report Vol. 24, No. 3, June (1978)] and an electric resistance-decreasing type [Japanese patent application Kokai (Laid-open) No. 18947/80] with increasing humidity.

In the case of a dew sensor of alternating current type, an electrolyte such as a chloride or a phosphate is used in the humidity-sensitive layer. However, such dew sensor has a more complicated circuit than that of direct current type, particularly when it is applied to a small, light appliance, for example, a portable VTR, and thus is not preferable for such use.

On the other hand, in the case of a dew sensor of direct current type, (a) conductor powder, (b) semiconductor powder or (c) insulator powder is used together with organic polymer in the humidity-sensitivie layer, where the powder is dispersed in the organic polymer or is in mixture of the organic powder [said Japanese patent application Kokai (Laid-open) No. 18947/80 and National Technical Report Vol. 24, No. 3 June (1978)], and thus has such a disadvantage as slow response to dewing detection owing to the dispersed or mixed state.

A dew sensor of resistance-increasing type with increasing humidity has a low resistance at the ordinary relative humidity (95% RH or lower) such as 10 kΩ, and the humidity-sensitivie layer is liable to generate the Joule heat, resulting in deterioration of the sensor. It has such a further disadvantage that the applicable voltage is limited to less than 0.8 V.

The cylinder of VTR is most susceptible to dewing due to a sudden change in temperature, etc., and once dews are formed on the cylinder, such troubles as sticking and winding of a tape to and around a cylinder, etc. are liable to take place, and thus it has been keenly desired that a dew sensor can quickly and sharply detect dewing, that is, without any substantial change in resistance in a low relative humidity range, in other words, with a sharp change in resistance in a RH range of 95–100% and a quick response to dewing. The sharp change in resistance and quick response to dewing can eliminate maloperation of a dew sensor. The conventional dew sensors have hardly satisfied these requirements.

SUMMARY OF THE INVENTION

An object of the present invention is to provide a dew sensor of direct current type and resistance-lowering type with increasing humidity for quickly and sharply detecting dewing with a sharp decrease in resistance in a RH range of 95 to 100% and quick response to dewing without the said disadvantages of the prior art.

The present invention provides a dew sensor which comprises a pair of counterposed electrodes, a humidity-sensitive layer of insulating porous metal oxide with a porosity of 20 to 60% provided on and between the counterposed electrodes, and an organic polymer coating layer having a thickness of 0.05 to 2 μm provided on the humidity-sensitive layer.

Furthermore, the present invention provides a dew sensor which comprises a substrate, a pair of counterposed electrodes provided on the substrate, a humidity-sensitive layer of insulating porous metal oxide with a porosity of 20 to 60% provided on and between the counterposed electrodes, and an organic polymer coating layer having a thickness of 0.05 to 2 μm provided on the humidity-sensitive layer.

The present dew sensor is prepared in the following manner.

Counterposed electrodes are metallic wires or plates of, for example, Au, Pt, Pd, etc., or those prepared by screen-printing an electroconductive paste of Au, Pt, Pd, or $RuO_2$ onto an insulating substrate of ceramics, etc. and firing the printed paste. The counterposed electrodes can have various shapes such as a straight form, curved form, spiral form, or comb form. The distance between the counterposed electrodes is usually 0.3–1.0 mm, and the electrode length is usually 5–50 mm.

$TiO_2$, $Al_2O_3$, $SiO_2$, $ZrO_2$, $BaTiO_3$, $SrTiO_3$, etc. are deposited on and between the counterposed electrodes as an insulating porous metal oxide acting as a humidity-sensitive material. The insulating porous metal oxide can contain a small amount of a semi-conductor oxide such as NiO, ZnO, $MnO_2$, etc. and a conductor oxide such as $RuO_2$, so long as the resulting mixture still has an insulating property. The insulating porous metal oxide is deposited to cover the counterposed electrodes and the spaces between the electrodes, and sintered to form a humidity-sensitive layer of porous metal oxide having a porosity of 20–60%.

Then, a solution of an organic polymer such as a cellulose derivative, for example, ethyl cellulose, methyl cellulose, and acetyl cellulose in a solvent is applied onto the humidity-sensitive layer of said porous metal oxide, and dried to form an organic polymer coating layer. The application can be carried out usually by dipping, spraying, spinning, etc. The organic polymer coating layer usually has a thickness of 0.05–2 μm.

When the porosity of the humidity-sensitive layer of insulating porous metal oxide is less than 20% or more than 60%, it has been experimentally found that the dewing is hard to detect rapidly (low response speed), as shown in the following Examples.

The present invention will be described in detail, referring to Examples and the accompanying drawings.

PREFERRED EMBODIMENTS OF THE INVENTION

Example 1

Figure 1:
FIG. 1 is a cross-sectional view showing one embodiment of the dew sensors according to Example 1.
Figure 2:
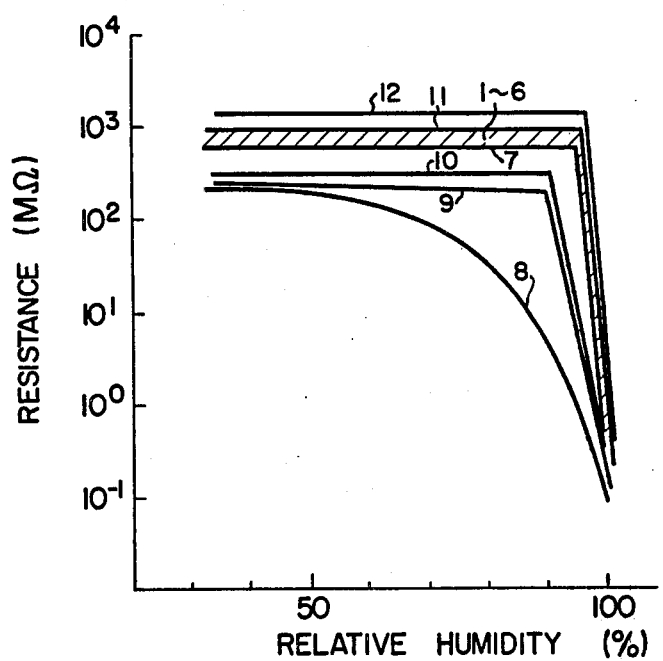
FIG. 2 is a diagram showing the relations between the relative humidity and the resistance of the dew sensors of Example 1.

Counterposed electrodes 1 were formed with Pt wires having a diameter of 0.2 mm and a length of 30 mm at a distance of 0.5 mm therebetween, as shown in FIG. 1. A layer 2 of $BaTiO_3$-based oxide was molded around the counterposed electrodes 1 to surround the electrodes. The oxide contained 3 to 9% by weight of $Bi_2O_3$-$B_2O_3$-$SiO_2$ glass on the basis of the oxide to promote sintering the oxide, and 10% by weight of an aqueous 3% polyvinyl alcohol solution on the basis of the total of the oxide and the glass to facilitate molding. The resulting molding was sintered at various temperatures ranging from 600° to 950° C. to form sintered $BaTiO_3$ having a porosity shown in Table 1 as a humidity-sensitive layer. No organic matters were contained in the sintered $BaTiO_3$ molding. The sintered $BaTiO_3$ molding was dipped in ethyl cellulose solutions in α-terpineol having various concentrations shown in Table 1, and dried at 170° C. for 30 minutes to form an ethyl cellulose coating layer 3. The thickness of coating layer was determined by dipping a glass plate into the same ethyl cellulose solutions in α-terpineol as used above, drying the glass plate under the same conditions as above, and measuring the thickness of the resulting ethyl cellulose film on the glass plate according to the ordinary surface measuring equipment. The time of response to dewing by the thus prepared dew sensors is shown in Table 1, which is a duration from the time of placing in a vessel kept at 25° C. and 75% RH the dew sensors cooled to 0° C. to the time of the resistance of dew sensors having reached less than 2 MΩ. Relations between the relative humidity and the resistance of dew sensors are shown in FIG. 2, and the resistance of dew sensors was determined by applying a direct current of 5 V to a circuit comprising a dew sensor and a resistor of 1 MΩ connected to the dew sensor in series, reading a voltage applied to the resistor of 1 MΩ by a voltmeter, and calculating the resistance of the sensor from the reading. The dew sensor numbers in Table 1 and FIG. 2 are identical with one another.

As is obvious from these results, there is a correlation between the porosity of sintered $BaTiO_3$ layer and the time of response to dewing. With the ethyl cellulose coating layers having a thickness of 0.3 μm, a good response time such as not more than 3.5 minutes can be obtained within the porosity range of 20 to 60%, and also the relations between the relative humidity and the resistance are practically satisfactory.

When the porosity is less than 20% or more than 60%, the response time becomes more than 5 minutes, and thus is not practical.

There is also a correlation between the thickness of ethyl cellulose coating layer on the sintered $BaTiO_3$ layer and the time of response to dewing. With the sintered $BaTiO_3$ having a porosity of 40%, the time of response to dewing is longer, with increasing thickness of ethyl cellulose coating layer. However, when the thickness of ethyl cellulose coating layer is very small, such as 0.03 μm, the resistance at a higher relative humidity than 95% RH is less than 2 MΩ, and also fails to take a sharp decrease, as shown by curve 8 in FIG. 2, resulting in increased occurrence of maloperation as a dew sensor. Thus, it is necessary for the present dew sensor that the ethyl cellulose coating layer has a thickness of 0.05–2 μm.

Substantially equal results were obtained with $TiO_2$ or $Al_2O_3$ as the porous metal oxide in place of $BaTiO_3$, and with methyl cellulose, or acetyl cellulose as the organic polymer in place of ethyl cellulose.

TABLE 1

| Dew sensor No. | Glass added (wt. %) | Sintering temp. of $BaTiO_3$ (°C.) | Porosity of sintered $BaTiO_3$ (%) | Ethyl cellulose concentration in dipping solution (wt. %) | Thickness of ethyl cellulose layer (μm) | Dewing response time (min.) |
|---|---|---|---|---|---|---|
| 1* | 9 | 950 | 15 | 5 | 0.3 | 5.5 |
| 2 | 8 | 900 | 20 | " | " | 3.5 |
| 3 | 7 | 800 | 30 | " | " | 2.0 |
| 4 | 6 | 700 | 40 | " | " | 1.5 |
| 5 | 5 | 650 | 50 | " | " | 2.0 |
| 6 | 4 | 600 | 60 | " | " | 3.5 |
| 7* | 3 | 600 | 65 | " | " | 5.5 |
| 8* | 6 | 700 | 40 | 0.5 | 0.03 | 0.5 |
| 9 | " | " | " | 1.0 | 0.05 | 0.6 |
| 10 | " | " | " | 2.5 | 0.1 | 0.8 |
| 11 | " | " | " | 9 | 1.0 | 2.5 |
| 12 | " | " | " | 12 | 2.0 | 4.5 |

Note:
Dew sensors having the number with an asterisk are outside the scope of the present invention.

Example 2

Figure 3:
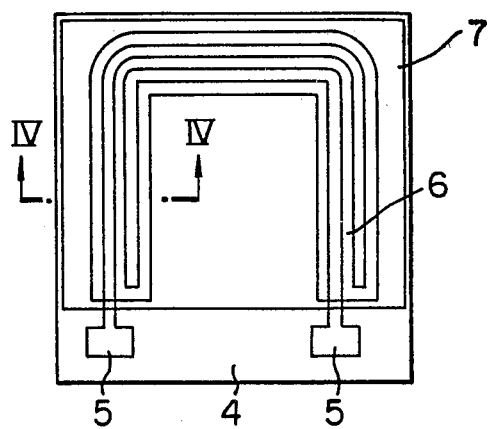
FIG. 3 is a plan view of another embodiment of the dew sensors according to Example 2.
Figure 4:
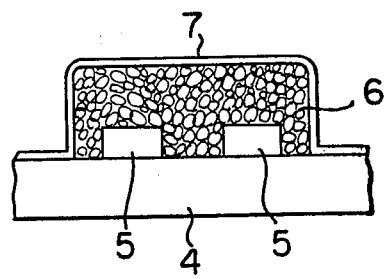
FIG. 4 is a cross-sectional view along the line IV—IV of FIG. 3.

A conductor paste containing Au and glass frit was printed onto an alumina substrate 4 having a size of 15×15×0.8 mm, and fired to form counterposed electrodes 5 having a length of 30 mm and a width of 0.5 mm at a distance of 0.5 mm between the electrodes, as shown in FIGS. 3 and 4. Then, a paste comprising $BaTiO_3$ and an organic vehicle was screen-printed on and between the counterposed electrodes to cover them, and sintered at various temperatures of 650° to 1,050° C., shown in Table 2 to form sintered $BaTiO_3$ layers having various porosities shown in Table 2 to obtain a humidity-sensitive layer. The $BaTiO_3$ paste contained 3 to 9% by weight of $Bi_2O_3$-$B_2O_3$-$SiO_2$ glass to promote sintering. The organic vehicle was a 5 wt. % ethyl cellulose solution in α-terpineol, and was used in an amount of 30% by weight on the basis of the total of BaTiO$_2$ and the glass to obtain a screen-printable paste. The sintering was carried out at a temperature of 650° to 1,050° C., and thus no organic matters remained in the sintered BaTiO$_3$ layer. The sintered BaTiO$_3$ layer had a thickness of about 60 μm.

Figure 5:
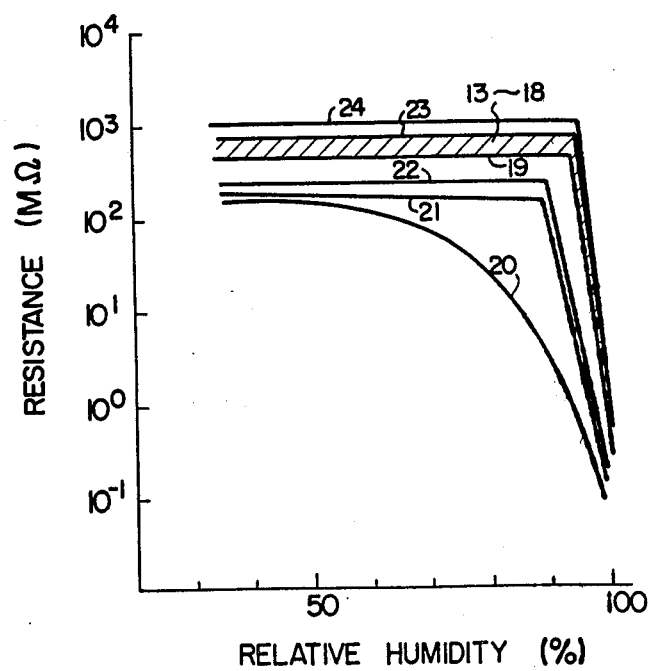
FIG. 5 is a diagram showing relations between the relative humidity and the resistance of the dew sensors of Example 2.

Then, the substrate with the sintered BaTiO$_3$ layer was dipped in ethyl cellulose solutions in α-terpineol having various ethyl cellulose concentrations shown in Table 2 and dried at 170° C. for 30 minutes to form an ethyl cellulose coating layer 7. The characteristics of the thus prepared dew sensors were determined in the same manner as in Example 1. The results are shown in Table 2 and FIG. 5, where the dew sensor numbers in Table 1 and FIG. 2 are identical with one another.

As is obvious from these results, there is a correlation between the porosity of sintered BaTiO$_3$ layer and the time of response to dewing. With the ethyl cellulose coating layers having a thickness of 0.3 μm, a good response time such as not more than 3.0 minutes can be obtained within the porosity range of 20 to 60%, and also the relations between the relative humidity and the resistance are practically satisfactory. When the porosity is less than 20% or more than 60%, the response time becomes more than 5 minutes, and thus is not practical.

There is also a correlation between the thickness of ethyl cellulose coating layer on the sintered BaTiO$_3$ layer and the time of response to dewing. With the sintered BaTiO$_3$ having a porosity of 40%, the time of response to dewing is longer with increasing thickness of ethyl cellulose coating layer. However, when the thickness of ethyl cellulose coating layer is very small, such as 0.03 μm, the resistance at a higher relative humidity than 90% RH is less than 2 MΩ, and also fails to take a sharp decrease, as shown by curve 20 in FIG. 5, resulting in increased occurrence of maloperation as a dew sensor. Thus, it is necessary for the present dew sensor that the ethyl cellulose coating layer has a thickness of 0.05-2 μm.

Substantially equal results were obtained with TiO$_2$ or Al$_2$O$_3$ as the porous metal oxide in place of BaTiO$_3$, and with methyl cellulose, or acetyl cellulose as the organic polymer in place of ethyl cellulose.

As described above, a practical dew sensor having a sharp change in resistance and a quick response to deposition of dews, that is dewing, in other words, a sharp decrease in resistance in a relative humidity range of 95 to 100% RH and a short time of response to dewing of less than 5 minutes without maloperation can be provided according to the present invention.

What is claimed is:

1. A dew sensor which comprises a pair of counterposed electrodes, a humidity-sensitive layer of insulating porous metal oxide with a porosity of 20 to 60% provided on and between the counterposed electrodes, and an organic polymer coating layer having a thickness of 0.05 to 2 μm provided on the humidity-sensitive layer.

2. A dew sensor which comprises a substrate, a pair of counterposed electrodes provided on the substrate, a humidity-sensitive layer of insulating porous metal oxide with a porosity of 20 to 60% provided on and between the counterposed electrodes, and an organic polymer coating layer having a thickness of 0.05 to 2 μm provided on the humidity-sensitive layer.

3. The dew sensor according to claim 1 or 2, wherein the organic polymer coating layer is comprised of cellulose derivative.

4. The dew sensor according to claim 3, wherein the cellulose derivative is ethyl cellulose, methyl cellulose or acetyl cellulose.

5. A dew sensor comprising a pair of counterposed electrodes; a humidity-sensitive layer, including an insulating porous metal oxide, with a porosity of 20 to 60% provided on and between the counterposed electrodes; and an organic polymer coating layer having a thickness of 0.05 to 2 μm provided on the humidity-sensitive layer, to thereby provide a dew sensor with a sharp decrease in resistance in a RH range of 95 to 100% and a response time of 5 minutes or less.

6. The dew sensor according to claim 5, wherein said pair of counterposed electrodes are positioned on a substrate.

7. The dew sensor according to claim 5 or 6, wherein said organic polymer coating layer is comprised of cellulose derivative.

8. The dew sensor according to claim 7, wherein said insulating porous metal oxide is selected from the group consisting of TiO$_2$, Al$_2$O$_3$, SiO$_2$, ZrO$_2$, BaTiO$_3$ and SrTiO$_3$.

9. The dew sensor according to claim 8, wherein said humidity-sensitive layer is formed by sintering the insulating porous metal oxide, said humidity-sensitive layer further including glass to promote the sintering.

10. The dew sensor according to claim 1, 2, 5 or 6, wherein said humidity-sensitive layer is formed by sintering the insulating porous metal oxide, said humidity-sensitive layer further including glass to promote the sintering.

11. The dew sensor according to claim 1, 2, 5 or 6, wherein the distance between the counterposed electrodes is 0.3–1.0 mm.

TABLE 2

| Dew sensor No. | Glass added (wt. %) | Sintering temp. of BaTiO$_3$ (°C.) | Porosity of sintered BaTiO$_3$ (%) | Ethyl cellulose concentration in dipping solution (wt. %) | Thickness of ethyl cellulose layer (μm) | Dewing response time (min.) |
|---|---|---|---|---|---|---|
| 13* | 9 | 1050 | 15 | 5 | 0.3 | 5.0 |
| 14 | 8 | 1000 | 20 | " | " | 3.0 |
| 15 | 7 | 900 | 30 | " | " | 1.5 |
| 16 | 6 | 800 | 40 | " | " | 1.0 |
| 17 | 5 | 700 | 50 | " | " | 1.5 |
| 18 | 4 | 650 | 60 | " | " | 3.0 |
| 19* | 3 | 650 | 65 | " | " | 5.0 |
| 20* | 6 | 800 | 40 | 0.5 | 0.03 | 0.4 |
| 21 | " | " | " | 1.0 | 0.05 | 0.5 |
| 22 | " | " | " | 2.5 | 0.1 | 0.7 |
| 23 | " | " | " | 9 | 1.0 | 2.0 |
| 24 | " | " | " | 12 | 2.0 | 4.0 |

Note:
Dew sensors having the number with an asterisk are outside the scope of the present invention.